United States Patent
Cho

(10) Patent No.: US 8,475,451 B2
(45) Date of Patent: Jul. 2, 2013

(54) MEDICAL PLASMA GENERATOR AND ENDOSCOPE USING THE SAME

(75) Inventor: Guang-sup Cho, Seoul (KR)

(73) Assignee: Kwangwoon University Industry-Academic Collaboration Foundation, Seoul (KR)

( * ) Notice: Subject to any disclaimer, the term of this patent is extended or adjusted under 35 U.S.C. 154(b) by 323 days.

(21) Appl. No.: 13/024,552

(22) Filed: Feb. 10, 2011

(65) Prior Publication Data

US 2011/0301412 A1    Dec. 8, 2011

(30) Foreign Application Priority Data

Jun. 8, 2010    (KR) .................. 10-2010-0053845
Nov. 29, 2010   (KR) .................. 10-2010-0119493

(51) Int. Cl.
*A61B 18/18* (2006.01)

(52) U.S. Cl.
USPC .................. 606/42; 600/114; 315/111.21

(58) Field of Classification Search
USPC .............. 606/41, 42, 46; 315/111.01, 111.11, 315/111.21, 341, 349, 350, 351; 600/101, 600/114

See application file for complete search history.

(56) References Cited

U.S. PATENT DOCUMENTS

| 5,597,456 | A * | 1/1997 | Maruyama et al. | 204/165 |
|---|---|---|---|---|
| 6,475,217 | B1 * | 11/2002 | Platt | 606/49 |
| 6,958,063 | B1 * | 10/2005 | Soll et al. | 606/41 |
| 8,105,325 | B2 * | 1/2012 | Suslov | 606/45 |
| 8,109,928 | B2 * | 2/2012 | Suslov | 606/45 |
| 8,337,494 | B2 * | 12/2012 | Suslov | 606/45 |
| 2011/0140607 | A1 * | 6/2011 | Moore et al. | 315/111.21 |
| 2012/0283732 | A1 * | 11/2012 | Lam | 606/49 |

* cited by examiner

*Primary Examiner* — Thuy Vinh Tran
(74) *Attorney, Agent, or Firm* — KED & Associates LLP

(57) ABSTRACT

A medical plasma generator and its application are provided. In the medical plasma generator, a gas supply tube supplies a gas required for the generation of plasma. An internal electrode in a tube shape has a joined part joined to the end of the gas supply tube, and an extended part extended from the joined part. The extended part has a smaller diameter than the joined part, thereby allowing the gas to jet out with an increased speed when the gas passes through the internal electrode. A high voltage is applied to the internal electrode. A glass tube encloses the extended part of the internal electrode and protruding from the internal electrode. A ground electrode is formed on an outer surface of a protruding part of the glass tube. Interaction between the ground electrode and the internal electrode leads to ionization and discharge of the gas passing through the internal electrode, thereby generating plasma. A tubular cover covers the glass tube and is extended beyond the glass tube. The medical plasma generator may be used alone or in combination with medical equipment such as en endoscope.

20 Claims, 14 Drawing Sheets

(a)    (b)

(a)    (b)

MEDICAL PLASMA GENERATOR AND ENDOSCOPE USING THE SAME

This application claims priority to Korean Patent Application No 10-2010-0053845 filed Jun. 8, 2010, and Korean Patent Application No. 10-2010-0119493 filed Nov. 29, 2010, whose entire disclosures are incorporated herein by reference.

BACKGROUND

1. Field

The present disclosure relates in general to an apparatus for generating plasma and, more particularly, to a medical plasma generator and its application for producing plasma and irradiating it onto a human body for the purpose of treatment or care.

2. Description of the Related Art

Normally a plasma generator is an apparatus in which gaseous molecules are separated into positive ions and negative electrons between cathode and anode electrodes to which a high frequency or a high voltage is applied. In this plasma generator, the electrodes may be installed in a vacuum state or in the atmosphere. Nowadays plasma generators are widely applied to a great variety of fields such as a semiconductor, a printed circuit board (PCB), synthesis of advanced materials, a surface treatment of polymer, a surface treatment of metal, environmental cleanup, medical instrument, sterilization and disinfection of groceries, and the like.

Plasma generators specially used for medical services are mostly atmospheric plasma generators that produce plasma at atmospheric pressure. The atmospheric plasma generator is effective for sterilization since chemical species such as atomic oxygen or OH radical in plasma oxidizes cell walls of germs. In addition, plasma is used for a nucleon destruction of bacterial cells, hemostasis and coagulation of blood, stimulation and repair of skin, removal of skin debris, teeth bleaching, athlete's foot, abscess, skin cancer, boils, and the like. High-energy plasma may be used for a surgical treatment that burns off human tissue.

In particular, a medical plasma generator should ensure its safety since it directly irradiates plasma onto a human body. For example, it is required to prevent an electric shock caused by a leakage of a high-voltage current used for the generation of plasma. Additionally, an easy and reliable control or regulation of plasma emission and irradiation is required to prevent physical injury and also to allow the use in a surgical treatment.

Furthermore, a medical plasma generator needs a great convenience in use and a reduction in size. Particularly, miniaturization for easy handling and a simple control of plasma emission are essential in applying a plasma generator to an endoscope.

BRIEF SUMMARY

Accordingly, the present disclosure is to address the above-mentioned problems and/or disadvantages and to offer at least the advantages described below.

One aspect of the present disclosure is to provide a medical plasma generator with a good safety, a great convenience in use and a reduction in size.

Another aspect of the present disclosure is to provide a medical plasma generator that can uniformly generate plasma and also can control the amount of plasma emission.

Still another aspect of the present disclosure is to provide a medical plasma generator that can prevent an electric shock caused by a leakage of a high-voltage current used for the generation of plasma.

Yet another aspect of the present disclosure is to provide a medical plasma generator that is miniaturized for easy handling and to be applicable to an endoscope.

Further aspect of the present disclosure is to provide an endoscope using a medical plasma generator.

According to one aspect of the present disclosure, provided is a medical plasma generator that comprises a gas supply tube, an internal electrode, a glass tube, and a ground electrode. The gas supply tube supplies a gas required for the generation of plasma. The internal electrode has a tube shape, a joined part joined to the end of the gas supply tube, and an extended part extended from the joined part. The extended part has a smaller diameter than the joined part, thereby allowing the gas to jet out with an increased speed when the gas passes through the internal electrode. A high voltage is applied to the internal electrode. The glass tube encloses the extended part of the internal electrode and protruding from the internal electrode. The ground electrode is formed on an outer surface of a protruding part of the glass tube. Interaction between the ground electrode and the internal electrode leads to ionization and discharge of the gas passing through the internal electrode, thereby generating plasma.

In the medical plasma generator, the extended part may include a conical part extended from the joined part and having a gradually narrowing diameter, and a straight part extended from the conical part and having a reduced uniform diameter.

In the medical plasma generator, the straight part may have one of a slant profile, a right-angled profile, and a sharp rim at an end part thereof.

In the medical plasma generator, the glass tube may be joined to an outer surface of the straight part.

In the medical plasma generator, the glass tube may be spaced apart from the outer surface of the straight part and joined to an outer surface of the conical part.

The medical plasma generator may further comprise an insulating layer interposed between the glass tube and the extended part.

In the medical plasma generator, the ground electrode may be formed in a ring shape on the outer surface of the protruding part of the glass tube beyond the internal electrode.

The medical plasma generator may further comprise an insulating protective layer is formed over the ground electrode.

The medical plasma generator may further comprise a power supply unit for supplying high-voltage AC power with a low frequency to the internal electrode.

In the medical plasma generator, the power supply unit may supply AC power with a frequency of several tens or hundreds of kilohertz and with a voltage of several hundred volts or several kilovolts to the internal electrode.

In the medical plasma generator, the power supply unit may include a switching mode power supply (SMPS) for converting commonly used AC power into DC power with a voltage of several volts, and a DC-AC inverter for receiving DC power from the SMPS, converting the received DC power into AC power with a frequency of several tens or hundreds of kilohertz and with a voltage of several hundred volts or several kilovolts, and then supplying the converted AC power to the internal electrode.

In the medical plasma generator, the DC-AC inverter may adjust or maintain the amount of current used for the generation of plasma by using a pulse width modulation method through a feedback circuit.

The medical plasma generator may further comprise a tubular cover covering the glass tube and the end of the gas supply tube, being extended beyond the glass tube, and having a plasma emitting hole for allowing plasma emission from an outlet of the glass tube.

In the medical plasma generator, the tubular cover may have a number of gas exhaust holes formed around the plasma emitting hole.

In the medical plasma generator, the plasma emitting hole may have a greater diameter than the outlet of the glass tube.

The medical plasma generator may further comprise a flow meter for regulating a flow rate of the gas being supplied through the gas supply tube; a gas flow regulator installed on the tubular cover, connected to the flow meter, and regulating a flow rate of the gas in the glass tube by controlling the flow meter; a voltage regulator installed on the tubular cover, connected to the SMPS, and regulating a voltage of DC power outputted from the SMPS to the DC-AC inverter; a high voltage line connected at one end thereof to the internal electrode, running along the gas supply tube, and connected at the other end thereof to the DC-AS inverter; a ground line connected to at one end thereof to the ground electrode, running along the gas supply tube, and connected at the other end thereof to the power supply unit; a flow meter connection line connected to at one end thereof to the gas flow regulator, running along the gas supply tube, and connected at the other end thereof to the flow meter; an SMPS connection line connected to at one end thereof to the voltage regulator, running along the gas supply tube, and connected at the other end thereof to the SMPS; and a sheath covering and protecting the gas supply tube, the high voltage line, the ground line, the flow meter connection line and the SMPS connection line.

In the medical plasma generator, the inside diameter of the glass tube may be below several centimeters. The length of the joined part of the internal electrode may be several centimeters. The ground electrode may have a ring shape with a width of several millimeters or several centimeters. And a distance from the end of the internal electrode to the end of the glass tube may be several millimeters or several centimeters.

In the medical plasma generator, the glass tube may have an outlet for allowing plasma emission. The outlet is smaller in the inside diameter than the other parts of the glass tube.

In the medical plasma generator, the glass tube may have the outlet curved inwardly thus narrowing its diameter, or an auxiliary tubular member inserted into and joined to the outlet.

According to another aspect of the present disclosure, provided is an endoscope that comprises the medical plasma generator set forth above, and a flexible insertion tube that is configured to be flexibly inserted into a person's body, accommodates the medical plasma generator therein, and has an end surface from which a part of the medical plasma generator is protruded to emit plasma.

Other aspects, advantages, and salient features of the disclosure will become apparent to those skilled in the art from the following detailed description, which, taken in conjunction with the annexed drawings, and disclosed embodiments of the disclosure.

DETAILED DESCRIPTION OF THE DRAWINGS

Exemplary, non-limiting embodiments of the present disclosure will now be described more fully with reference to the accompanying drawings. This disclosure may, however, be embodied in many different forms and should not be construed as limited to the exemplary embodiments set forth herein. Rather, the disclosed embodiments are provided so that this disclosure will be thorough and complete, and will fully convey the scope of the disclosure to those skilled in the art. The principles and features of this disclosure may be employed in varied and numerous embodiments without departing from the scope of the disclosure.

Furthermore, well known or widely used techniques, elements, structures, and processes may not be described or illustrated in detail to avoid obscuring the present disclosure. Although the drawings represent exemplary embodiments of the disclosure, the drawings are not necessarily to scale and certain features may be exaggerated or omitted in order to better illustrate and explain the present disclosure.

Figure 1:
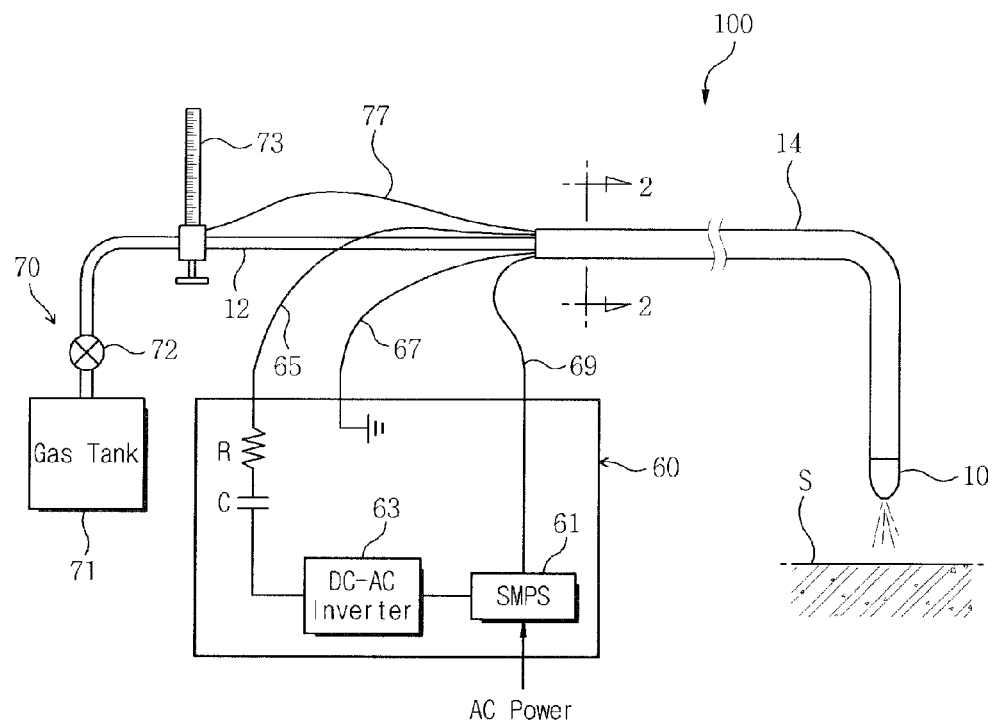
FIG. 1 is a schematic view illustrating a medical plasma generator in accordance with an embodiment of the present disclosure.

FIG. 1 is a schematic view illustrating a medical plasma generator in accordance with an exemplary embodiment of the present disclosure. And FIG. 2 is a cross-sectional view illustrating a gas supply tube shown in FIG. 1.

Figure 2:
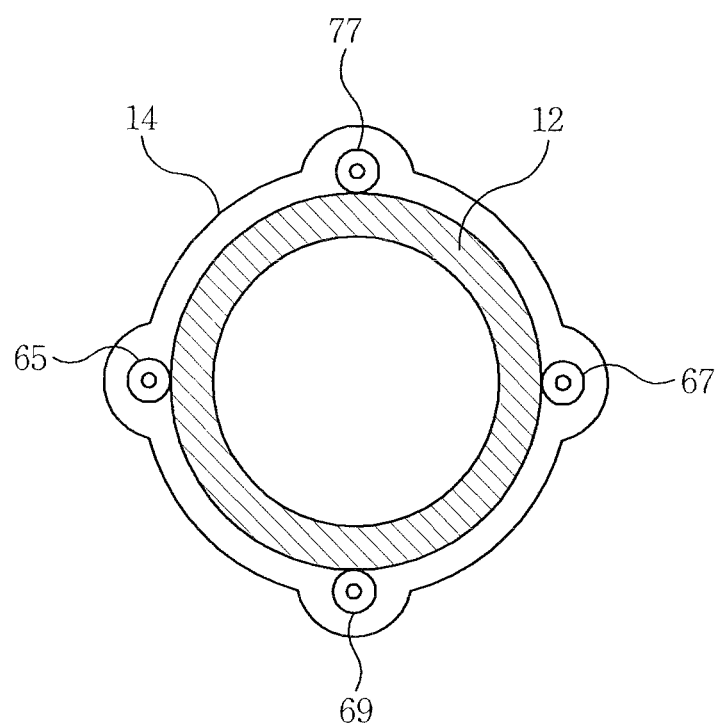
FIG. 2 is a cross-sectional view illustrating a gas supply tube shown in FIG. 1.

Referring to FIGS. 1 and 2, the medical plasma generator 100 includes a power supply unit 60, a gas supply unit 70, and a plasma generating unit 10. The power supply unit 60 supplies alternating current (AC) power with a low frequency required for the generation of plasma to the plasma generating unit 10. The gas supply unit 70 supplies a gas required for the generation of plasma to the plasma generating unit 10. Then the plasma generating unit 10 generates plasma by applying AC power with a low frequency to a gas and then emits the plasma to a treatment target (S).

The power supply unit 60 converts commonly used AC power (60 Hz, 100 or 220 V) into AC power with a frequency of several tens or hundreds of kilohertz and with a voltage of several hundred volts or several kilovolts and then supplies the converted AC power to the plasma generating unit 10. The power supply unit 60 includes a switching mode power supply (SMPS) 61 and a DC-AC inverter 63. The SMPS 61 converts commonly used AC power into direct current (DC) power with a voltage of several volts. The DC-AC inverter 63 receives DC power from the SMPS 61, converts the received DC power into AC power with a frequency of several tens or hundreds of kilohertz and with a voltage of several hundred volts or several kilovolts, and then supplies the converted AC power to the plasma generating unit 10 through a high voltage line 65.

The DC-AC inverter 63 may adjust or maintain the amount of current used for the generation of plasma by using a well-known pulse width modulation (PWM) method through a feedback circuit.

A ground electrode (40 shown in FIG. 3) of the plasma generating unit 10 is connected to the power supply unit 60 through a ground line 67 and thereby grounded. The SMPS 61 adjusts the voltage of DC power to be inputted to the DC-AD inverter 63 according to a control signal received from the plasma generating unit 10 through an SMPS connection line 69.

AC power outputted from the DC-AC inverter 63 is supplied to the plasma generating unit 10 through a condenser (C) and a resistor (R). These condenser and resistor may prevent the amount of plasma and current from being rapidly increased in the plasma generating unit 10.

The gas supply unit 70 includes a gas tank 71 and a flow meter 73. The gas tank 71 stores a gas to be used for the generation of plasma. The flow meter 73 regulates a flow rate of a gas that flows from the gas tank 71 to the plasma generating unit 10. When regulating a gas flow rate, the flow meter 73 depends on a control signal received from the plasma generating unit 10 through a flow meter connection line 77. The gas tank 71 may have a valve 72 for opening or closing a gas supply port thereof. The gas tank 71 stores an argon (Ar) or helium (He) gas. The gas supplied to the plasma generating unit 10 may be a mixed gas of a carrier gas such as argon or helium and a reactant gas such as the air or oxygen. A reactant gas may be injected into a gas supply tube 12 between the gas tank 71 and the flow meter 73.

The plasma generating unit 10 is connected to the gas supply unit 70 including the gas tank 71 through the gas supply tube 12 and receives a gas through the gas supply tube 12. Namely, the gas supply tube 12 is connected at one end to the gas tank 71 and also connected at the other end to the plasma generating unit 10. The flow meter 73 is installed on the gas supply tube 12 near the gas tank 71 between the gas tank 71 and the plasma generating unit 10.

The gas supply tube 12 may be protected by a sheath 14. Additionally, the high voltage line 65, the ground line 67, the SMPS connection line 69 and the flow meter connection line 77 may be interposed between the gas supply tube 12 and the sheath 14. Although in this embodiment the high voltage line 65 is located on the exterior of the gas supply tube 12, the high voltage line 65 may be alternatively installed inside the gas supply tube 12.

Figure 3:
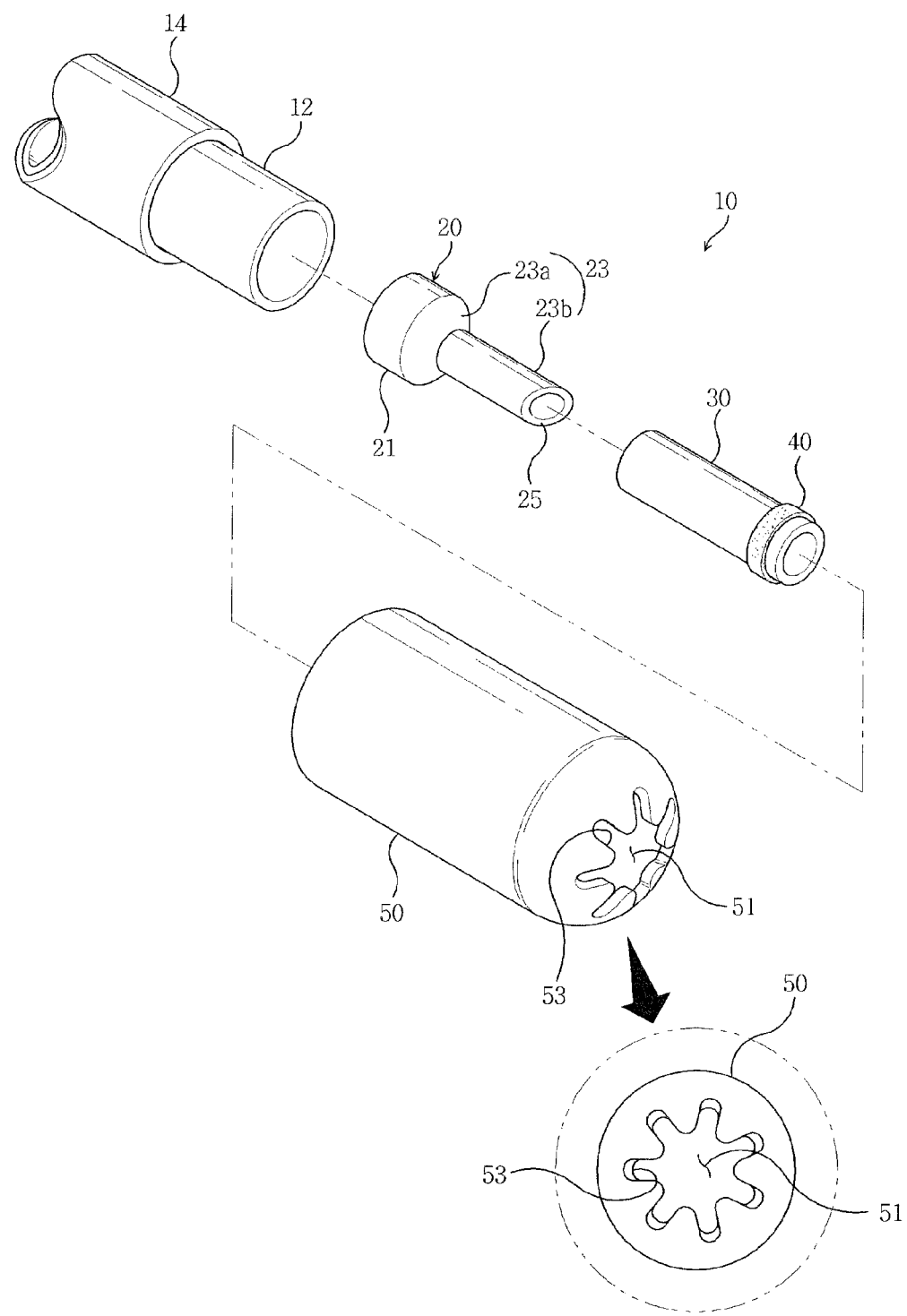
FIG. 3 is an exploded perspective view illustrating a plasma generating unit shown in FIG. 1.
Figure 4:
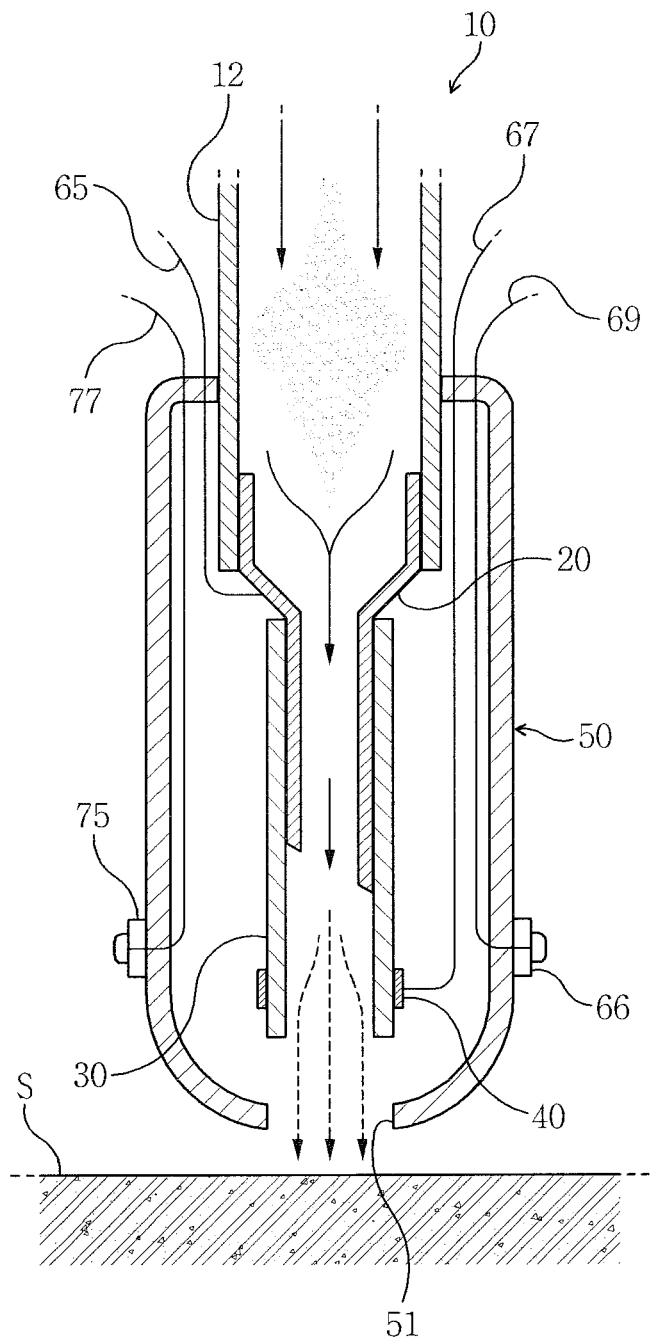
FIG. 4 is a cross-sectional view illustrating a plasma generating unit shown in FIG. 1.

Now, the plasma generating unit 10 will be more fully described with reference to FIGS. 1 to 4. FIG. 3 is an exploded perspective view illustrating the plasma generating unit shown in FIG. 1. And FIG. 4 is a cross-sectional view illustrating the plasma generating unit shown in FIG. 1.

The plasma generating unit 10 includes the gas supply tube 12, an internal electrode 20, a glass tube 30, and a ground electrode 40. The gas supply tube 12 allows the flow of a gas required for the generation of plasma. The internal electrode 20 has a tube shape and is joined at the first part thereof to the end of the gas supply tube 12. The second part of the internal electrode 20 is extended from the first part and has a smaller diameter than the first part has. A gas that exhausts through the gas supply tube 12 passes through the first and second parts of the internal electrode 20. A high voltage is applied to the second part of the internal electrode 20 through the high voltage line 65. The glass tube 30 encloses the second part of the internal electrode 20 and protrudes from the internal electrode 20. The ground electrode 40 is formed on the outer surface of the glass tube 30, especially on the protruding part of the glass tube 30. Interaction between the ground electrode 40 and the internal electrode 20 leads to ionization and discharge of a gas passing through the internal electrode 20, thus generating plasma. The plasma generating unit 10 may further include a tubular cover 50 that covers the end of the gas supply tube 12, the internal electrode 20, the glass tube 30, and the ground electrode 40.

As mentioned above, the gas supply tube 12 allows the flow of a gas for the generation of plasma. The gas supply tube 12 may be made of flexible Teflon material. Although in FIG. 4 both the internal electrode 20 and the tubular cover 50 are joined to the end of the gas supply tube 12 without the sheath 14, both 20 and 50 may be alternatively joined to the end of the gas supply tube 12 covered with the sheath 14.

As discussed above, in the tube-shaped internal electrode 20, the first part joined to the gas supply tube 12 has a greater diameter than the second part inserted into the glass tube 30. Namely, the internal electrode 20 has a funnel form. Hereinafter, the first and second parts of the internal electrode 20 will be referred to as a joined part 21 and an extended part 23, respectively. The joined part 21 is joined to the inner surface of the gas supply tube 12. The extended part 23 is extended from the joined part 21 and protrudes from the gas supply tube 12. The extended part 23 is composed of a conical part 23a and a straight part 23b. The conical part 23a has a gradually narrowing diameter, and the straight part 23b has a reduced uniform diameter. The high voltage line 65 may be connected to the conical part 23a. The internal electrode 20 may be made of metal or any other material with a good electric conductivity.

Figure 5:
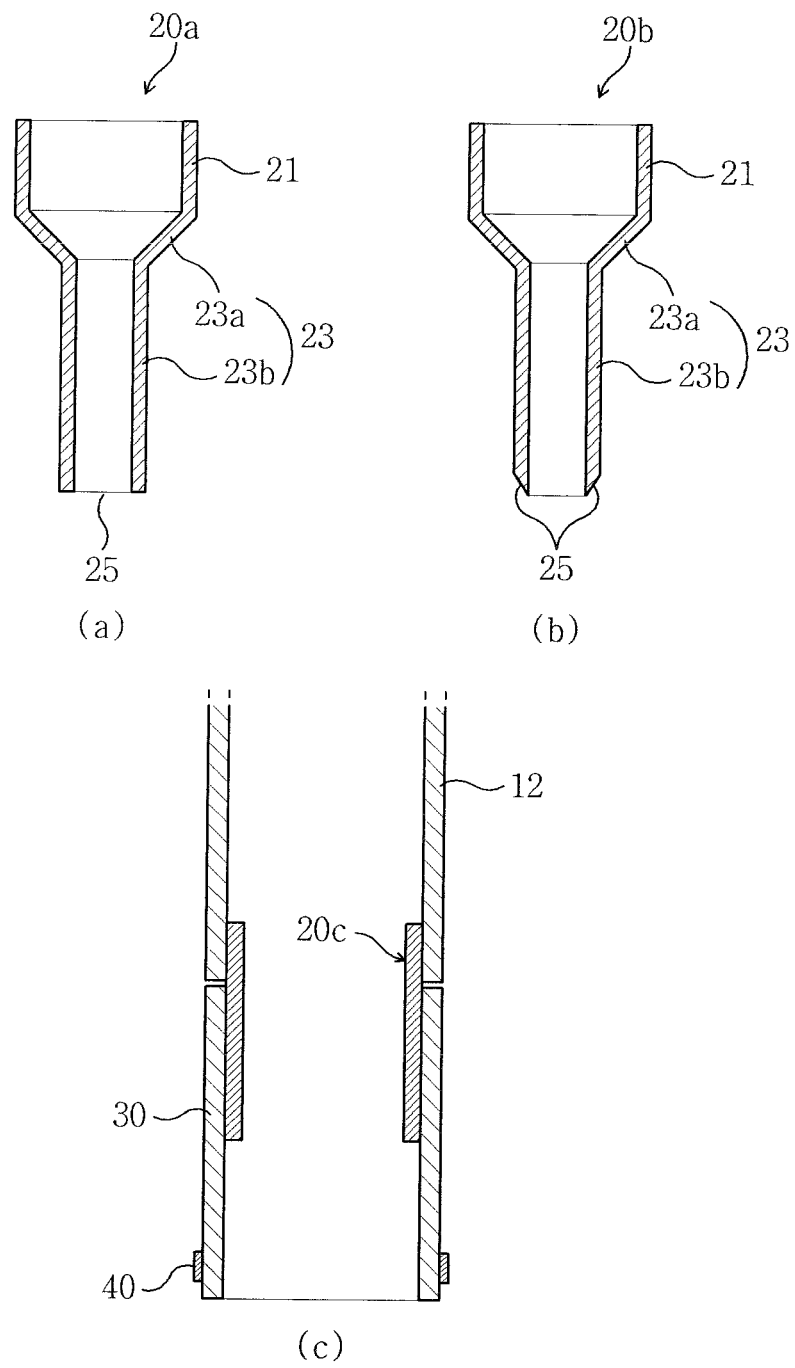
FIG. 5 is a cross-sectional view illustrating variations of an internal electrode shown in FIG. 1.

The reason that the diameter of the extended part 23 is smaller than that of the joined part 21 is to allow a gas to jet out with an increased speed through the extended part 23. Even if all parts of the internal electrode 20c have a uniform diameter as shown in FIG. 5(c), plasma is generated at a part of the glass tube 30 on which the ground electrode 40 is formed. However, in this case, since there is little difference in speed between an incoming gas from the gas supply tube 12 and an outgoing gas passing through the internal electrode 20c, namely since a jet of a gas passing through the internal electrode 20c is not made, a discharge voltage is excessively high and plasma is unfavorably spread backward from the internal electrode 20c. Also, the end of the internal electrode 20c may be damaged due to the use for a long time. For the above reasons, it is desirable that the extended part 23 of the internal electrode 20 has a smaller diameter than the joined part 21.

Meanwhile, although in this embodiment the internal electrode 20 is joined to the inner surface of the gas supply tube 12, the present disclosure is not limited to that. Alternatively, as exemplarily shown in FIG. 6, the joined part 21 of the internal electrode 20 may be joined to the outer surface of the gas supply tube 12. Namely, the end of the gas supply tube 12 may be inserted into and joined to the joined part 21 of the internal electrode 20.

Figure 8:
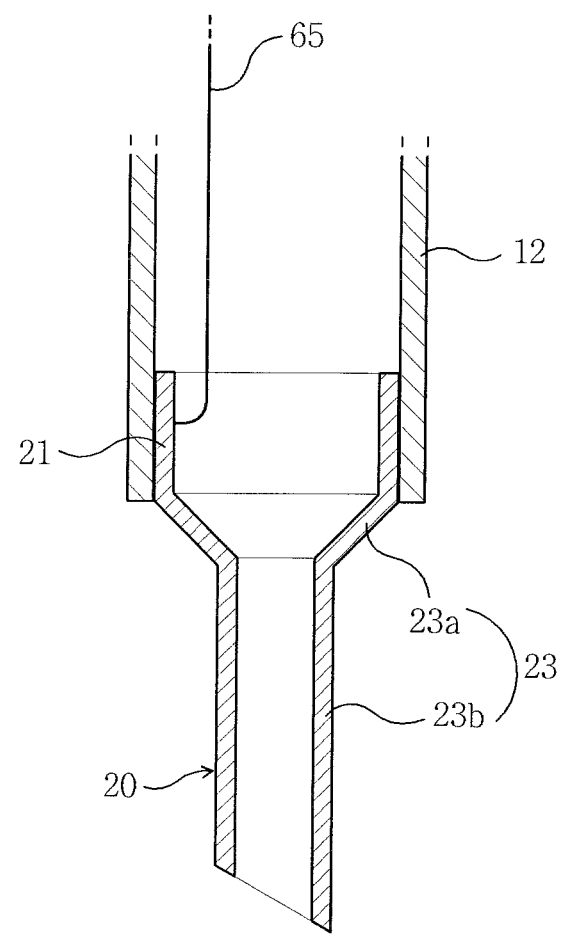
FIG. 8 is a cross-sectional view illustrating another example of a connection between an internal electrode and a high voltage line shown in FIG. 1.

Additionally, although in this embodiment the high voltage line 65 is connected to the outer surface of the conical part 23a of the internal electrode 20, the present disclosure is not limited to that. Alternatively, as exemplarily shown in FIG. 8, the high voltage line 65 may be connected to the inner surface of the joined part 21 of the internal electrode 20 through the interior of the gas supply tube 12.

Furthermore, although in this embodiment the end part 25 of the internal electrode 20 has a slant profile, the present disclosure is not limited to that. Alternatively, as exemplarily shown in FIG. 5(a), the end part 25 of the internal electrode 20a may have a right-angled profile. Also, as exemplarily shown in FIG. 5(b), the end part 25 of the internal electrode 20b may have a sharp rim.

Returning to FIGS. 1 to 4, the glass tube 30 is joined to the outer surface of the straight part 23b of the internal electrode 20 and protrudes from the straight part 23b. Little gap between the glass tube 30 and the straight part 23b is advantageous for a plasma discharge and also allows the plasma generating unit 10 to become slimmer. The inside diameter of the glass tube 30 may be almost equal to the external diameter of the straight part 23b. For instance, the inside diameter of the glass tube 30 may be determined according to the quantity of plasma and may be selected below several centimeters. Preferably, the glass tube 30 may be formed to have the inside diameter varying from several millimeters to several centimeters. If necessary, the glass tube 30 may have the inside diameter below one millimeter. The thickness of the glass tube 30 is below one millimeter. If possible, a smaller thickness within an endurable limit against a high voltage is advantageous for a plasma discharge. Preferably, the length of the joined part 21 of the internal electrode 20 is several centimeters. A distance from the end of the internal electrode 20 to the end of the glass tube 30 is several millimeters or several centimeters.

Figure 6:
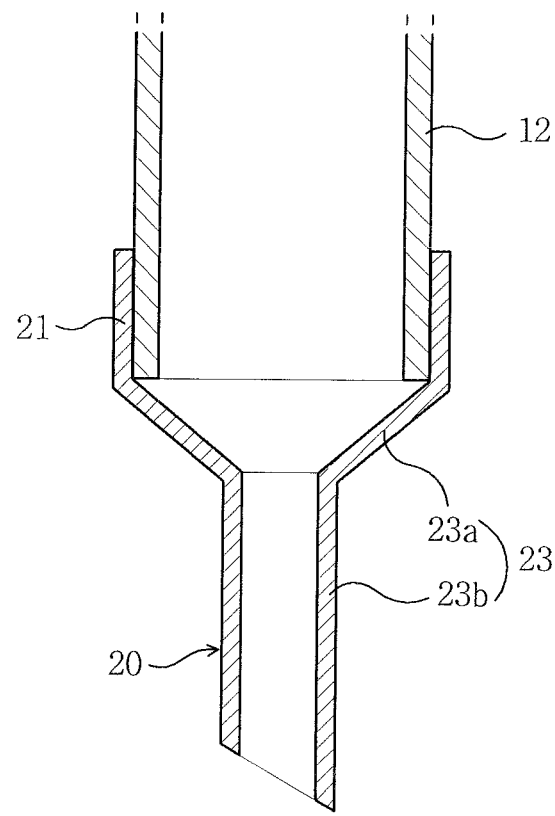
FIG. 6 is a cross-sectional view illustrating another example of a connection between an internal electrode and a gas supply tube shown in FIG. 1.
Figure 7:
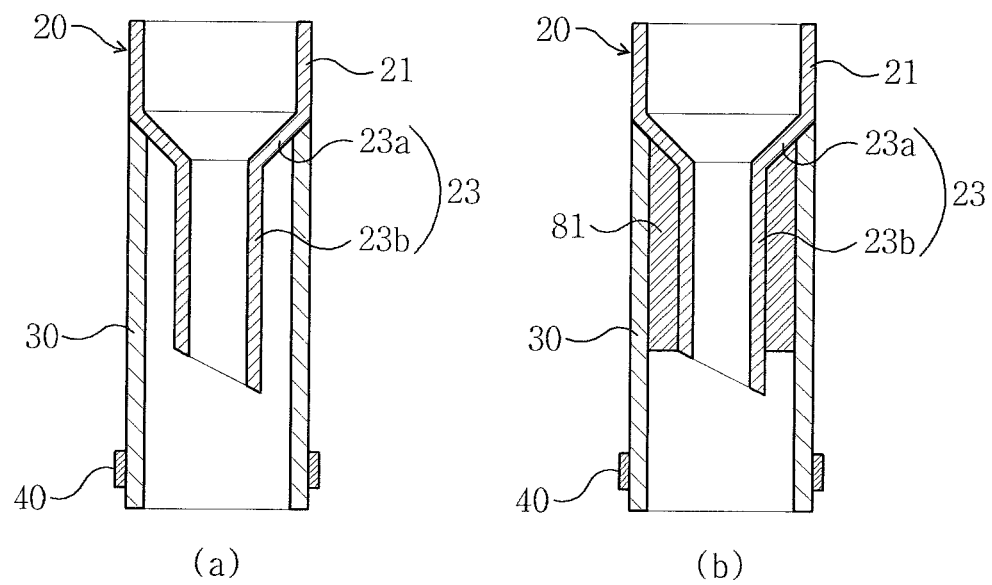
FIG. 7 is a cross-sectional view illustrating other examples of a connection between an internal electrode and a glass tube shown in FIG. 1.

Meanwhile, although in this embodiment the glass tube 30 is joined to the straight part 23b of the internal electrode 20, the present disclosure is not limited to that. Alternatively, as exemplarily shown in FIG. 7(a), the glass tube 30 may be joined to the outer surface of the conical part 23a of the internal electrode 20, while being spaced apart from the straight part 23b. In this case, as shown in FIG. 7(b), an insulating layer 81 may be interposed between the glass tube 30 and the internal electrode 20. If the end of the gas supply tube 12 is inserted into and joined to the joined part 21 of the internal electrode 20 as shown in FIG. 6, the glass tube may be joined to the outer surface of the joined part 21 with or without the insulating layer interposed therebetween. When the glass tube 30 is joined to the internal electrode 20 in various ways as discussed above, well-known insulating adhesive may be used for joining.

Returning to FIGS. 1 to 4, the ground electrode 40 is formed in a ring shape on the outer surface of the glass tube 30, especially on the protruding part of the glass tube 30 beyond the internal electrode 20, and then connected to the ground line 67. A coating, deposition or soldering of metal with a good conductivity may be used for forming the ground electrode 40 on the glass tube 30. For instance, the ground electrode 40 may have a ring shape with a width of several millimeters or several centimeters. In this embodiment, the ground electrode 40 is spaced apart from the internal electrode 20 on the glass tube 30.

When a high voltage is applied to the internal electrode 20, the electric field is created between the internal electrode 20 on the inner surface of the glass tube 30 and the ground electrode 40 on the outer surface of the glass tube 30. As a result, a gas that is passing through the internal electrode 20 is ionized and discharged, and therefore plasma is generated and then emitted through the end of the glass tube 30. The length of plasma emission may be adjusted according to a high voltage applied to the internal electrode 20 and a flow rate of a gas. Plasma emission from the end of the glass tube 30 may be several millimeters or several centimeters in length.

As discussed above, the internal electrode 20 having a funnel form is provided at the end of the gas supply tube 12, and also the ground electrode 40 is provided on the outer surface of the protruding part of the glass tube 30 enclosing the internal electrode 20. Interaction between the internal electrode 20 and the ground electrode 40 leads to ionization and discharge of a gas passing through the internal electrode 20, so that plasma can be reliably generated. In particular, since the ground electrode 40 is spaced apart from the internal electrode 20, plasma generated near the end of the glass tube 30 can be effectively emitted from the glass tube 30.

Figure 9:
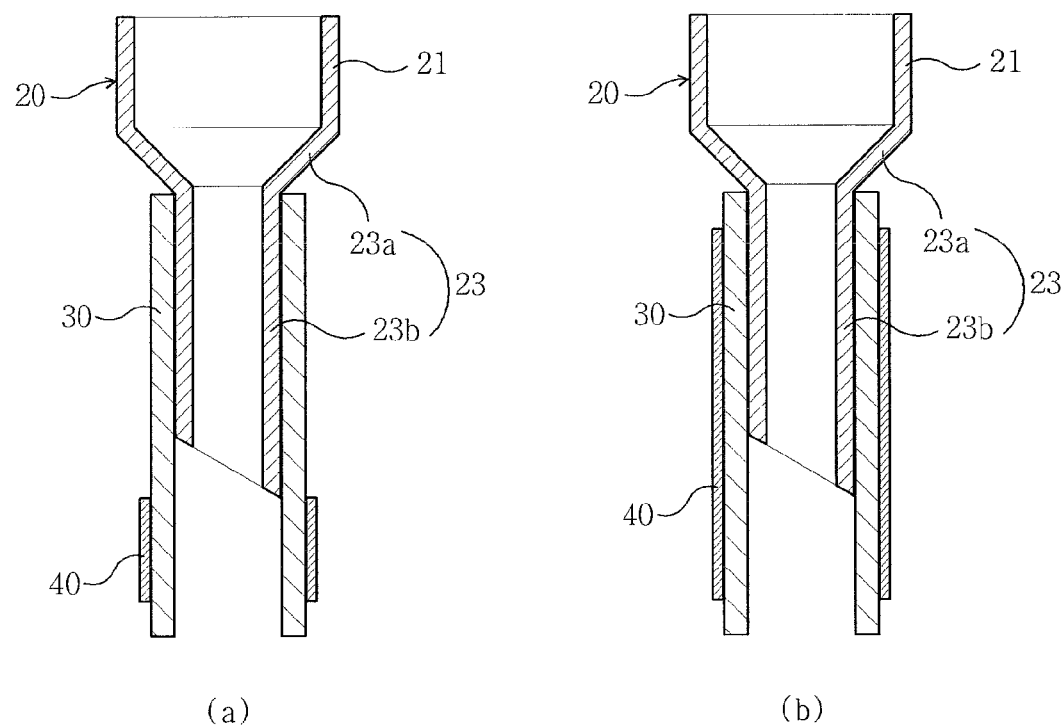
FIG. 9 is a cross-sectional view illustrating variations of a ground electrode formed on a glass tube shown in FIG. 1.

Although in this embodiment the ground electrode 40 is spaced apart from the internal electrode 20 in a lengthwise direction, the present disclosure is not limited to that. Alternatively, as exemplarily shown in FIG. 9(a), the ground electrode 40 may be somewhat extended on the glass tube 30 so as to approach the internal electrode 20. Additionally, as exemplarily shown in FIG. 9(b), the ground electrode 40 may be further extended on the glass tube 30 so as to partially cover the internal electrode 20.

Figure 10:
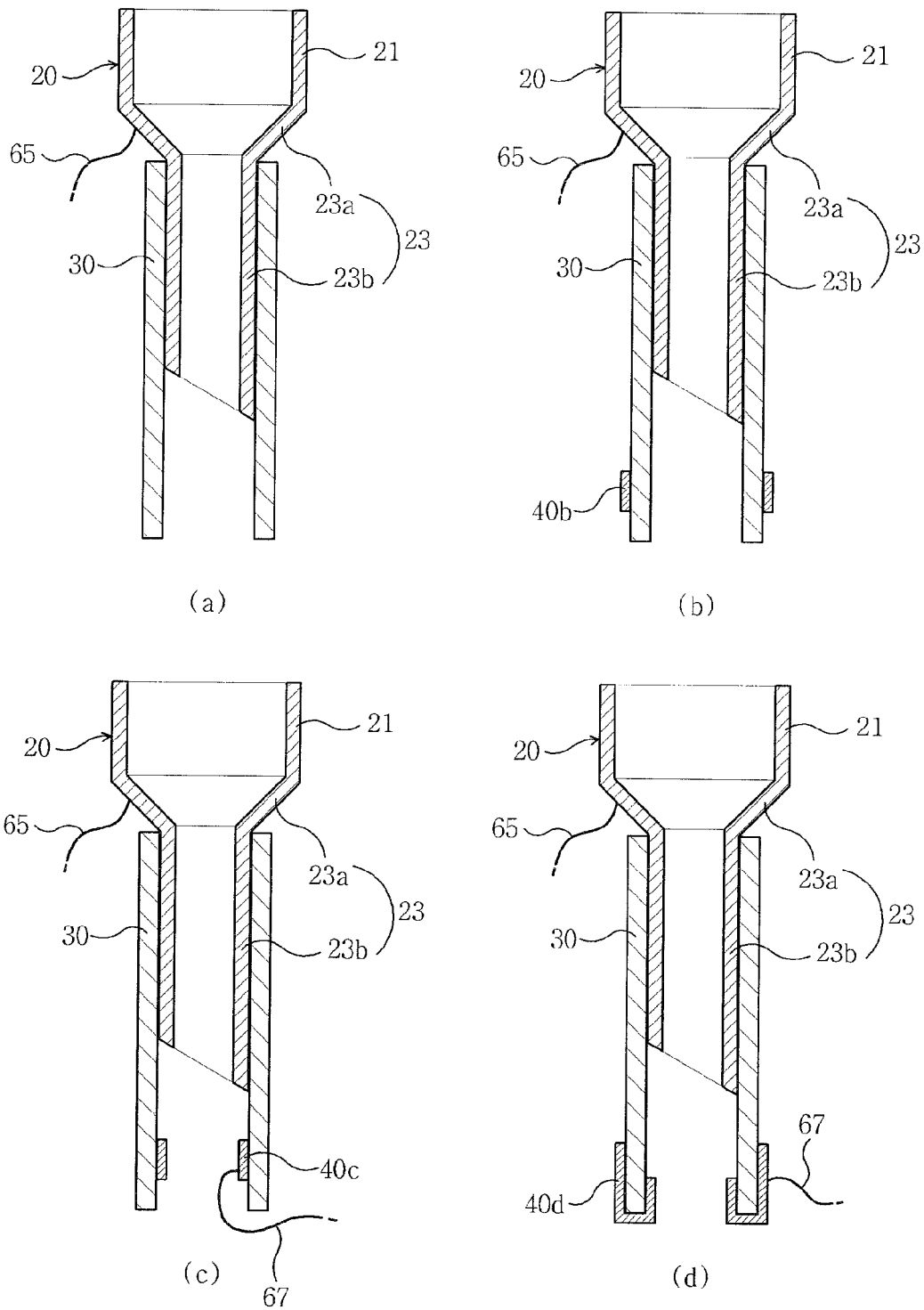
FIG. 10 is a cross-sectional view illustrating experimental examples of a ground electrode formed on a glass tube shown in FIG. 1.

However, as exemplarily shown in FIG. 10, the absence or some variations of the ground electrode 20 is undesirable in view of experimental results.

Specifically, when no ground electrode is formed on the glass tube 30 as shown in FIG. 10(a), or when the ground electrode 40b is present but not grounded as shown in FIG. 10(b), the discharge is not facilitated, and also it is difficult to control the generation of plasma. These problems are the same as in case where the ground electrode is located in the interior of the glass tube but not grounded.

Additionally, when the ground electrode 40c is formed on the inner surface of the glass tube 30 as shown in FIG. 10(c), or when the ground electrode 40d is extended from the inner surface to the outer surface of the glass tube 30 as shown in FIG. 10(d), the ground electrodes 40c and 40d are exposed to plasma. In these cases, plasma flows out in the form of current through the ground electrodes 40c and 40d, so that plasma cannot be emitted from the end of the glass tube 30.

If a cylindrical metal is used instead of both the glass tube and the ground electrode, plasma emission is impossible as can be confirmed through experiments. If the ground electrode is located within the glass tube or not grounded, it is difficult to adjust the amount of plasma emitted from the end of the glass tube.

In addition, by converting commonly used AC power into AC power with a frequency of several tens or hundreds of kilohertz and with a voltage of several hundred volts or several kilovolts and then applying the converted AC power to the internal electrode 20, the generation of plasma can be effectively realized. Also, by adjusting DC voltages applied to the DC-AC inverter 63, it is possible to obtain uniform plasma and to control the emission of plasma.

If high-frequency (MHz) RF power or microwave (GHz) power is used between the internal electrode 20 and the ground electrode 40, the amount of plasma is not adjustable and a reduction in size of a power supply unit is not possible.

Figure 11:
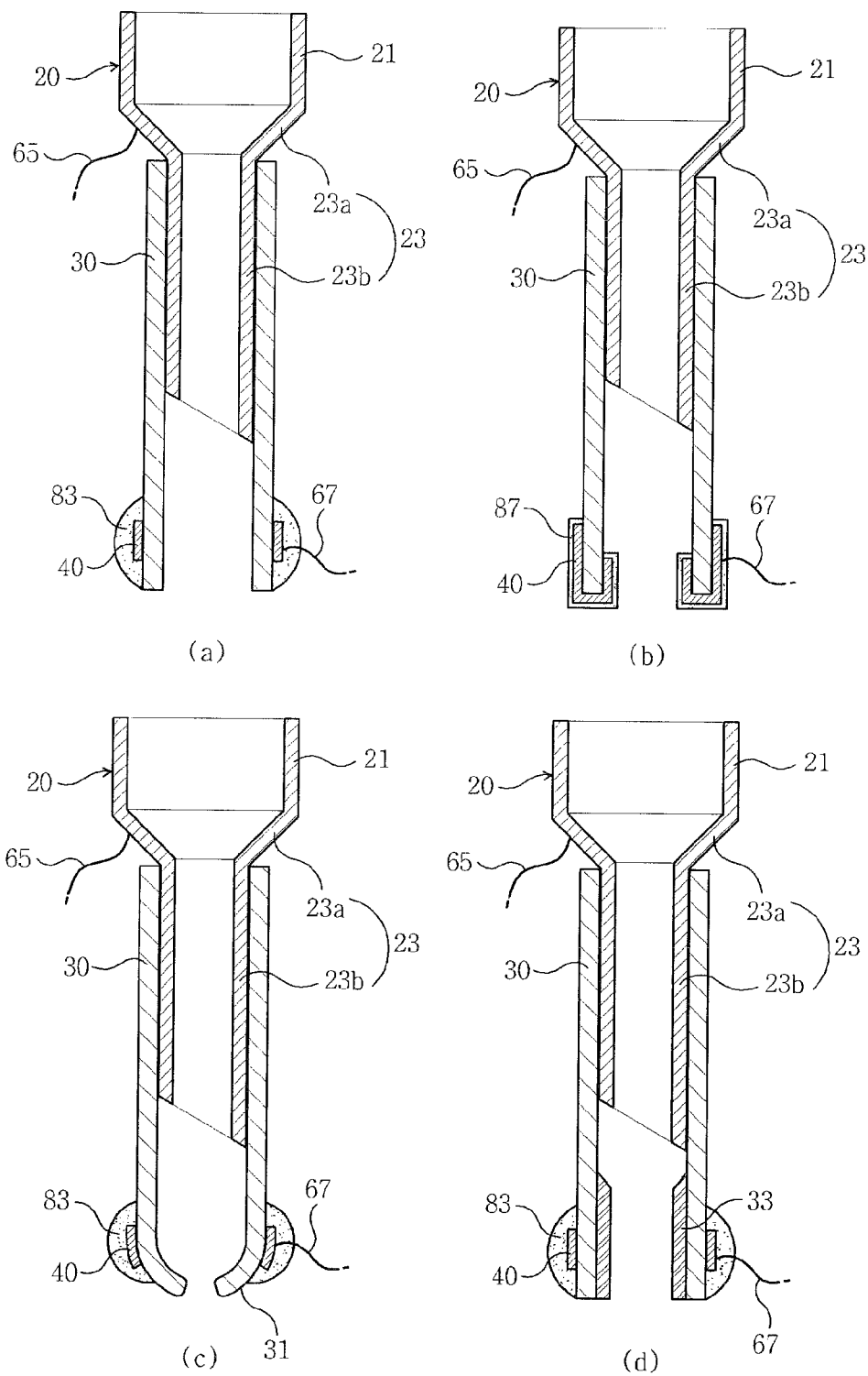
FIG. 11 is a cross-sectional view illustrating examples of an insulating protective layer covered on a ground electrode shown in FIG. 1.

Meanwhile, as shown in FIG. 11, an insulating protective layer 83 may be formed over the ground electrode 40.

As shown in FIG. 11(a), the insulating protective layer 83 may cover the ground electrode 40 formed on the outer surface of the glass tube 30. This insulating protective layer 83 can prevent plasma emitted through the glass tube 30 from undesirably flowing out through the ground electrode 40.

If the ground electrode 40 is extended to the inner surface of the glass tube 30 as shown in FIG. 11(b), the insulating protective layer 83 should cover the ground electrode 40 in order to allow an easy control of plasma emission. Normally when plasma directly contacts with the ground electrode 40, the amount of plasma current is rapidly increased and plasma drains away through the ground electrode. So, plasma emission is not accomplished.

In another example shown in FIG. 11(c), the ground electrode 40 is formed on the outer surface of the glass tube 30 and then covered with the insulating protective layer 83. Therefore, plasma emitted through the glass tube 30 can be prevented from undesirably flowing out through the ground electrode 40. Moreover, an outlet 31 of the glass tube 30 may be smaller in the inside diameter than the other parts of the glass tube 30. This shape of the outlet 31 may reduce the thickness of plasma being emitted and also extend the length of plasma emission. In this example, the outlet 31 of the glass tube 30 is curved inwardly while narrowing its diameter.

Additionally, as shown in FIG. 11(d), an auxiliary tubular member 33 is inserted into and joined to the outlet of the glass tube 30 so as to narrow the outlet of the glass tube 30. Therefore, the auxiliary tubular member 33 may reduce the thickness of plasma being emitted and also extend the length of plasma emission. The auxiliary tubular member 33 may be formed of glass or ceramic. In order to prevent vortex from occurring due to the collision between plasma and the front of the auxiliary tubular member 33, a front edge of the auxiliary tubular member 33 may slope. This slope edge of the auxiliary tubular member 33 may guide a smooth flow of plasma. While the auxiliary tubular member 33 is located on the inner surface of the glass tube 30, the ground electrode 40 covered with the insulating protective layer 83 is located on the outer surface of the glass tube 30 as discussed above.

Meanwhile, although structures for narrowing the outlet of the glass tube 30, that is, the inwardly curved outlet 31 shown in FIG. 11(c) or the auxiliary tubular member 33 shown in FIG. 11(d), are used for the glass tube 30 on which the insulating protective layer 83 is formed, the present disclosure is not limited to that. Such structures for narrowing the outlet of the glass tube 30 may be also applied to the glass tube 30 having no insulating protective layer thereon.

Returning to FIGS. 1 to 4, the tubular cover 50 is installed on the end of the gas supply tube 12 in order to cover the glass tube 30 as well as the end of the gas supply tube 12. The tubular cover 50 is extended beyond the end of the glass tube 30 and has a plasma emitting hole 51 that corresponds in position to the outlet of the glass tube 30. The plasma emitting hole 51 may have a greater diameter than the outlet of the glass tube 30 so that plasma can be reliably emitted. Additionally, a number of gas exhaust holes 53 are formed at regular intervals around the plasma emitting hole 51.

In order to allow plasma emitted from the end of the glass tube 30 to be irradiated onto the treatment target (S), a space should be secured between the end of the glass tube 30 and the treatment target (S). This is because the glass tube 30 may be occasionally clogged up with the treatment target (S) by an unintentional contact between the end of the glass tube 30 and the treatment target (S) and therefore the generation of plasma may be stopped. Moreover, if no space is secured between the end of the glass tube 30 and the treatment target (S), sudden variations of plasma emission during a treatment may give rise to an electric shock on the treatment target (S) such as skin texture of a human body. It is therefore desirable to use the tubular cover 50 in order to regularly maintain the amount of plasma irradiated onto the treatment target (S) and also to prevent unexpected electrical hazards. The tubular cover 50 is extended in several millimeters from the end of the glass tube 30 and then partially encloses the end of the glass tube 30. The gas exhaust holes 53 prevent the plasma emitting hole 51 from being clogged up with the treatment target (S) by offering escape paths of plasma even when the plasma emitting hole 51 is touched on the treatment target (S). For easy handling, the tubular cover 50 may be about ten centimeters in length and several centimeters in diameter.

In addition, a gas flow regulator 75 and a voltage regulator 66 may be installed on the outer surface of the tubular cover 50. The gas flow regulator 75 installed on the tubular cover 50 is connected to the flow meter 73 through the flow meter connection line 77. The gas flow regulator 75 regulates a flow rate of a gas in the glass tube 30 by controlling the flow meter 73. The voltage regulator 66 installed on the tubular cover 50 is connected to the SMPS 61 through the SMPS connection line 69. The voltage regulator 66 regulates a voltage of DC power outputted from the SMPS 61 to the DC-AC inverter 63. The gas flow regulator 75 and the voltage regulator 66 may be located at suitable positions for easy manipulations with the fingers when a user grips the tubular cover 50.

As discussed above, each of the high voltage line 65, the ground line 67, the SMPS connection line 69 and the flow meter connection line 77 is connected at one end thereof to the power supply unit 60 or the gas supply unit 70 and then runs along the gas supply tube 12 while being interposed between the gas supply tube 12 and the sheath 14. If the sheath 14 does not reach the end of the gas supply tube 12, the other ends of the above lines 65, 67, 69 and 77 may penetrate the front end of the tubular cover 50 and then be connected to the internal electrode 20, the ground electrode 40, the gas flow regulator 75 and the voltage regulator 66, respectively. If the sheath 14 is extended to the end of the gas supply tube 12 and therefore enters into the tubular cover 50, the other ends of the above lines 65, 67, 69 and 77 may be connected to their respective destinations 20, 40, 75 and 66 without penetrating the front end of the tubular cover 50.

Meanwhile, although in this embodiment the gas flow regulator 75 and the voltage regulator 66 are installed on the tubular cover 50, the present disclosure is not limited to that. If the medical plasma generator has separately a control box, the gas flow regulator and the voltage regulator may be provided in the control box.

Figure 12:
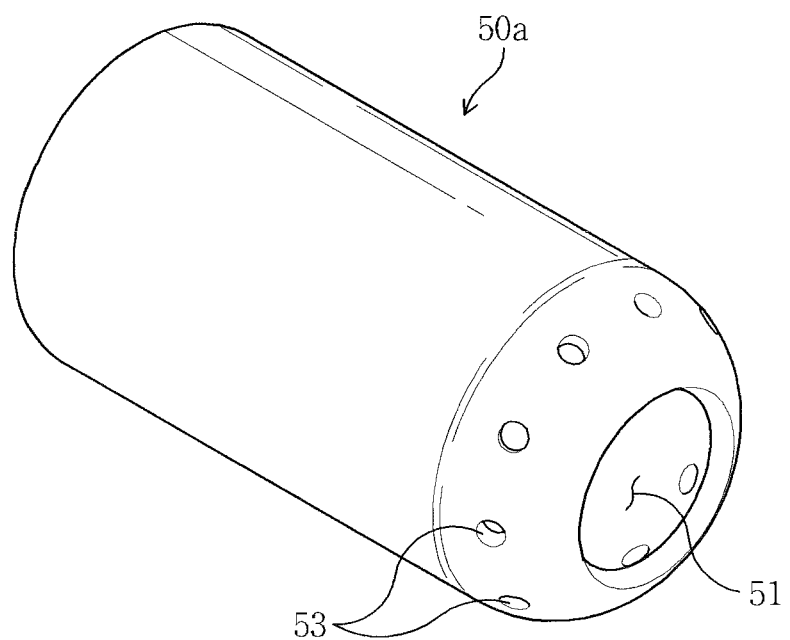
FIG. 12 is a perspective view illustrating another example of a tubular cover shown in FIG. 1.

Furthermore, although in this embodiment the tubular cover 50 has the gas exhaust holes 53 integrated with and extended from the plasma emitting hole 51, the present disclosure is not limited to that. Alternatively, as shown in FIG. 12, the tubular cover 50a may have a number of gas exhaust holes 53 that are formed separately from the plasma emitting hole 51. The gas exhaust holes 53 may be disposed at regular intervals around the plasma emitting hole 51 as shown or may be formed near a part of the circumference of the plasma emitting hole 51. Also, some of the gas exhaust holes 53 may be integrated with the plasma emitting hole 51, and the others may be separated from the plasma emitting hole 51.

As discussed above, since the glass tube 30 and the internal electrode 20 are protected by the tubular cover 50 and since the ground electrode 40 is protected by the insulating protective layer 83, unexpected accidents due to a high voltage used for the generation of plasma may be prevented favorably.

Additionally, since the tubular cover 50 has the gas exhaust holes 53 around the plasma emitting hole 51, the gas exhaust holes 53 may offer escape paths of plasma even when the plasma emitting hole 51 is kept in contact with the treatment target (S). Thus, the plasma emitting hole 51 may not be clogged up with the treatment target (S) and also a failure in plasma generation may be prevented favorably.

Furthermore, since the gas supply tube is covered with the tubular cover 50 and since the gas flow regulator 75 and the voltage regulator 66 are installed on the outer surface of the tubular cover 50, a user can easily and conveniently manipulate the medical plasma generator 100 as if to use a pen.

The medical plasma generator 100 according to the above-discussed embodiment operates as follows.

First of all, the user grips and moves the tubular cover 50 so that the plasma emitting hole 51 may approach the treatment target (S). Then a mixed gas of a reactant gas and a carrier gas is supplied through the gas supply tube 12, and also high-voltage AC power with a low frequency is applied to the internal electrode 20. At this time, a gas flowing through the internal electrode 20 having a funnel form is jetted out with an increased speed.

When a high voltage is applied to the internal electrode 20, the electric field is created between the internal electrode 20 and the ground electrode 40. A gas jetted from the end of the internal electrode 20 is ionized and discharged, thus generating plasma.

The plasma goes through the glass tube 30 by a flow of a gas and is then irradiated onto the treatment target (S) through the plasma emitting hole 51 of the tubular cover 50. At this time, chemical species such as O, OH and O3 created by plasma, ions in plasma, and ultraviolet rays are irradiated onto the treatment target (S) such as skin or teeth so that the treatment target (S) can be cured.

The aforesaid medical plasma generator 100 may be used alone or in combination with any other medical equipment. As exemplarily shown in FIGS. 13 and 14, an endoscope assembly 200 may use the medical plasma generator 100 fully discussed hereinbefore. Namely, since the plasma generating unit 10 has an external diameter similar to that of the gas supply tube 12, the medical plasma generator 100 can be reduced in size and applicable to an endoscope 90.

Figure 13:
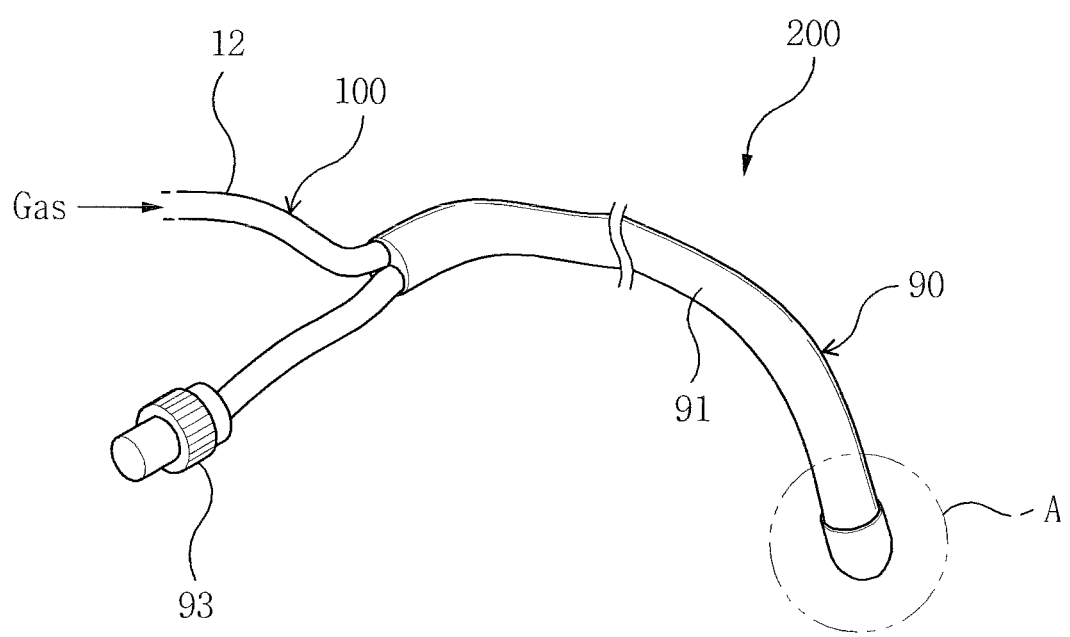
FIG. 13 is a perspective view illustrating an endoscope assembly using the medical plasma generator shown in FIG. 1.
Figure 14:
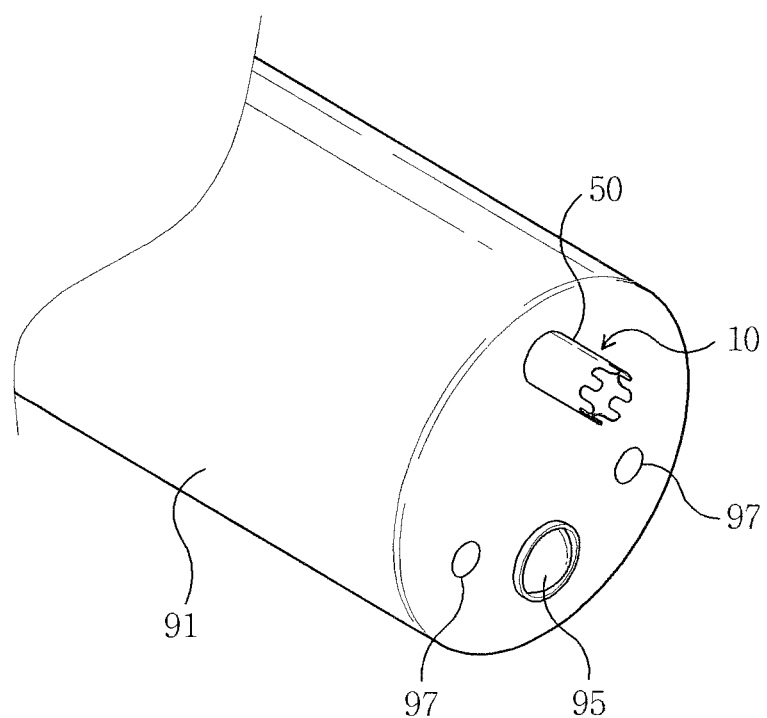
FIG. 14 is an enlarged view illustrating a section A of FIG. 13.

As shown in FIGS. 13 and 14, the endoscope assembly 200 includes the endoscope 90 in which the medical plasma generator 100 is combined, and an endoscope regulator 93. The endoscope 90 is composed of the medical plasma generator 100 and a flexible insertion tube 91. The plasma generating unit 10, a camera lens 95 and a light source 97 are provided on and in the end surface of the flexible insertion tube 91.

The plasma generating unit 10 of the medical plasma generator 100 is accommodated in the flexible insertion tube 91 and partly protruded from the end surface of the flexible insertion tube 91. The tubular cover 50 of the plasma generating unit 10 may be retracted into the flexible insertion tube 91 when plasma is not irradiated. Namely, the plasma generating unit 10 may move back and forth from the end surface of the flexible insertion tube 91. Additionally, a suction (not shown) for removing a gas may be further installed in the flexible insertion tube 91.

The endoscope regulator 93 controls the medical plasma generator 100, the camera lens 95, the light source 97, or the like, depending on user's manipulations.

With the flexible insertion tube 91 put into a person's body, the user can see images of the treatment target taken by the camera lens 95 and then use plasma for remedy while controlling the endoscope regulator 93.

While this disclosure has been particularly shown and described with reference to an exemplary embodiment thereof, it will be understood by those skilled in the art that various changes in form and details may be made therein without departing from the spirit and scope of the disclosure as defined by the appended claims.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

What is claimed is:

1. A medical plasma generator comprising:
a gas supply tube for supplying a gas required for the generation of plasma;
an internal electrode having a tube shape, a joined part joined to the end of the gas supply tube, and an extended part extended from the joined part, wherein the extended part has a smaller diameter than the joined part, thereby allowing the gas to jet out with an increased speed when the gas passes through the internal electrode, and wherein a high voltage is applied to the internal electrode;
a glass tube enclosing the extended part of the internal electrode and protruding from the internal electrode; and
a ground electrode formed on an outer surface of a protruding part of the glass tube, wherein interaction between the ground electrode and the internal electrode leads to ionization and discharge of the gas passing through the internal electrode, thereby generating plasma.

2. The medical plasma generator of claim 1, wherein the extended part includes:
a conical part extended from the joined part and having a gradually narrowing diameter; and
a straight part extended from the conical part and having a reduced uniform diameter.

3. The medical plasma generator of claim 2, wherein the straight part has one of a slant profile, a right-angled profile, and a sharp rim at an end part thereof.

4. The medical plasma generator of claim 2, wherein the glass tube is joined to an outer surface of the straight part.

5. The medical plasma generator of claim 2, wherein the glass tube is spaced apart from the outer surface of the straight part and joined to an outer surface of the conical part.

6. The medical plasma generator of claim 5, further comprising:
an insulating layer interposed between the glass tube and the extended part.

7. The medical plasma generator of claim 1, wherein the ground electrode is formed in a ring shape on the outer surface of the protruding part of the glass tube beyond the internal electrode.

8. The medical plasma generator of claim 7, further comprising:
an insulating protective layer is formed over the ground electrode.

9. The medical plasma generator of claim 7, wherein the inside diameter of the glass tube is below several centimeters, wherein the length of the joined part of the internal electrode is several centimeters, wherein the ground electrode has a ring shape with a width of several millimeters or several centimeters, and wherein a distance from the end of the internal electrode to the end of the glass tube is several millimeters or several centimeters.

10. The medical plasma generator of claim 1, further comprising:
a power supply unit for supplying high-voltage AC power with a low frequency to the internal electrode.

11. The medical plasma generator of claim 10, wherein the power supply unit supplies AC power with a frequency of several tens or hundreds of kilohertz and with a voltage of several hundred volts or several kilovolts to the internal electrode.

12. The medical plasma generator of claim 10, wherein the power supply unit includes:
a switching mode power supply (SMPS) for converting commonly used AC power into DC power with a voltage of several volts; and
a DC-AC inverter for receiving DC power from the SMPS, converting the received DC power into AC power with a frequency of several tens or hundreds of kilohertz and with a voltage of several hundred volts or several kilovolts, and then supplying the converted AC power to the internal electrode.

13. The medical plasma generator of claim 12, wherein the DC-AC inverter adjusts or maintains the amount of current used for the generation of plasma by using a pulse width modulation method through a feedback circuit.

14. The medical plasma generator of claim 12, further comprising:
a tubular cover covering the glass tube and the end of the gas supply tube, being extended beyond the glass tube, and having a plasma emitting hole for allowing plasma emission from an outlet of the glass tube.

15. The medical plasma generator of claim 14, wherein the tubular cover has a number of gas exhaust holes formed around the plasma emitting hole.

16. The medical plasma generator of claim 14, wherein the plasma emitting hole has a greater diameter than the outlet of the glass tube.

17. The medical plasma generator of claim 14, further comprising:
a flow meter for regulating a flow rate of the gas being supplied through the gas supply tube;
a gas flow regulator installed on the tubular cover, connected to the flow meter, and regulating a flow rate of the gas in the glass tube by controlling the flow meter;
a voltage regulator installed on the tubular cover, connected to the SMPS, and regulating a voltage of DC power outputted from the SMPS to the DC-AC inverter;
a high voltage line connected at one end thereof to the internal electrode, running along the gas supply tube, and connected at the other end thereof to the DC-AS inverter;
a ground line connected to at one end thereof to the ground electrode, running along the gas supply tube, and connected at the other end thereof to the power supply unit;
a flow meter connection line connected to at one end thereof to the gas flow regulator, running along the gas supply tube, and connected at the other end thereof to the flow meter;
an SMPS connection line connected to at one end thereof to the voltage regulator, running along the gas supply tube, and connected at the other end thereof to the SMPS; and
a sheath covering and protecting the gas supply tube, the high voltage line, the ground line, the flow meter connection line and the SMPS connection line.

18. The medical plasma generator of claim 1, wherein the glass tube has an outlet for allowing plasma emission, the outlet being smaller in the inside diameter than the other parts of the glass tube.

19. The medical plasma generator of claim 18, wherein the glass tube has the outlet curved inwardly thus narrowing its diameter, or an auxiliary tubular member inserted into and joined to the outlet.

20. An endoscope comprising:
the medical plasma generator set forth in one of claim 1; and
a flexible insertion tube configured to be flexibly inserted into a person's body, accommodating the medical plasma generator therein, and having an end surface from which a part of the medical plasma generator is protruded to emit plasma.

* * * * *